(12) United States Patent
Choi et al.

(10) Patent No.: US 9,297,725 B2
(45) Date of Patent: Mar. 29, 2016

(54) APPARATUS FOR EXTRACTING, ANALYZING, AND STORING GAS IN DRILLED CORE ON SHIP

(75) Inventors: Jiyoung Choi, Daejeon (KR); Jong-Hwa Chun, Daejeon (KR); Ji-Hoon Kim, Daejeon (KR); Jang Jun Bahk, Goyang-si (KR)

(73) Assignee: Korea Institute of Geoscience and Mineral Resources, Daejeon (KR)

(*) Notice: Subject to any disclaimer, the term of this patent is extended or adjusted under 35 U.S.C. 154(b) by 635 days.

(21) Appl. No.: 13/538,266

(22) Filed: Jun. 29, 2012

(65) Prior Publication Data

US 2013/0239672 A1  Sep. 19, 2013

(30) Foreign Application Priority Data

Mar. 13, 2012  (KR) .................. 10-2012-0025802

(51) Int. Cl.
*G01N 1/22* (2006.01)
*G01N 33/00* (2006.01)

(52) U.S. Cl.
CPC ............ *G01N 1/2226* (2013.01); *G01N 1/2294* (2013.01); *G01N 33/0009* (2013.01)

(58) Field of Classification Search
CPC .................. G01N 2001/2285; G01N 1/2294
USPC ............. 73/152.07, 152.09, 152.11, 863.81, 73/23.42, 23.38, 23.41, 23.35
See application file for complete search history.

(56) References Cited

U.S. PATENT DOCUMENTS

| | | | | |
|---|---|---|---|---|
| 2,632,512 | A * | 3/1953 | Chaney et al. | 166/100 |
| 3,685,345 | A * | 8/1972 | Wise | 73/19.1 |
| 3,868,970 | A * | 3/1975 | Ayers et al. | 137/625.46 |
| 4,350,051 | A * | 9/1982 | Thompson | 73/864.74 |
| 4,384,471 | A * | 5/1983 | Wentzel | 73/23.38 |
| 4,891,186 | A * | 1/1990 | Roberge et al. | 422/83 |
| 5,012,845 | A * | 5/1991 | Averette | 141/329 |
| 5,265,031 | A * | 11/1993 | Malczewski | 702/24 |
| 5,591,406 | A * | 1/1997 | Hirai et al. | 422/80 |
| 5,741,959 | A * | 4/1998 | Garcia et al. | 73/19.05 |
| 5,887,491 | A * | 3/1999 | Monson et al. | 73/864.74 |
| 5,922,974 | A * | 7/1999 | Davison et al. | 73/864.74 |
| 5,992,213 | A * | 11/1999 | Tartre | 73/19.01 |
| 6,038,934 | A * | 3/2000 | Peterson | 73/863.86 |
| 6,395,560 | B1 | 5/2002 | Markelov | |
| 7,240,535 | B2 * | 7/2007 | Wohltjen | 73/23.42 |
| 8,307,704 | B2 * | 11/2012 | Georgi et al. | 73/152.07 |
| 8,623,297 | B2 * | 1/2014 | Le Comte et al. | 422/512 |
| 2010/0161229 | A1 * | 6/2010 | Georgi et al. | 702/11 |

FOREIGN PATENT DOCUMENTS

| | | |
|---|---|---|
| JP | 10-260170 A | 9/1998 |
| JP | 11-76202 A | 3/1999 |
| JP | 2007-509323 A | 4/2007 |
| KR | 10-0978143 B1 | 8/2010 |
| KR | 10-1048528 B1 | 7/2011 |

* cited by examiner

*Primary Examiner* — John Fitzgerald
(74) *Attorney, Agent, or Firm* — Sughrue Mion, PLLC

(57) ABSTRACT

Provided is an apparatus for extracting, analyzing, and storing gas in a drilled core on a ship. The apparatus includes: a needle for core insertion inserted into the drilled core to allow the gas in the drilled core to the outside; and a first 3-way valve into which the gas passing through the needle for core insertion is introduced and which controls the introduced gas so as to be supplied to a gas storing container or gas analyzing apparatuses positioned on a ship.

2 Claims, 4 Drawing Sheets

APPARATUS FOR EXTRACTING, ANALYZING, AND STORING GAS IN DRILLED CORE ON SHIP

CROSS REFERENCE TO RELATED APPLICATION

This application is claiming priority based on Korean Patent Application No. 10-2012-0025802 filed Mar. 13, 2012, the contents of all of which are incorporated herein by reference in their entirety.

CROSS-REFERENCE TO RELATED APPLICATIONS

This application claims priority under 35 U.S.C. §119 to Korean Patent Application No. 10-2012-0025802, filed on Mar. 13, 2012, in the Korean Intellectual Property Office, the disclosure of which is incorporated herein by reference in its entirety.

TECHNICAL FIELD

The following disclosure relates to an apparatus for extracting and analyzing gas in a drilled core secured through ocean exploration.

BACKGROUND

Ocean exploration has been conducted in order to search for resources present on the seabed, such as petroleum, natural gas, and gas hydrate.

Generally, in an ocean exploration method, exploration of predicting whether or not seabed resources such as petroleum, natural gas, gas hydrate, and the like, is present using a seismic exploration method, an unmanned underwater vehicle, or the like, is preferentially performed.

The seismic exploration method is a method based on a feature that a transfer speed of a seismic wave in pure gas hydrate is faster than that of a seismic wave in a sedimentary layer, such that a transfer speed of the seismic wave in a sedimentary layer containing gas hydrate is faster than that of the seismic wave in a sedimentary layer not containing gas hydrate and a feature that a seismic wave chimney, or the like, is shown in a cross-sectional view of the seismic wave and gas hydrate, or the like, is present at an upper portion of the seismic wave chimney.

The exploration method using the unmanned underwater vehicle is a method of exploring whether or not gas hydrate is present by measuring concentrations of methane gas through injection of an exploration apparatus into the seabed since the methane gas is discharged in the case in which gas hydrate is present on the seabed.

Korean Patent No. 10-1048528 has suggested an exploration method using an unmanned underwater vehicle.

When it is determined by the seismic exploration method and the exploration method using an unmanned underwater vehicle as described above that the seabed resource such as gas hydrate or the like is present, a drilling apparatus descends to a seabed surface of a corresponding point to perform drilling, thereby directly confirming whether or not the seabed resource is present.

Korean Patent No. 10-0978143 has suggested a structure of an apparatus of drilling a seabed sediment.

A drilled core is filled with the seabed sediment through the drilling. Since the seabed sediment exist under relatively high temperature and low pressure conditions in a process in which the seabed sediment is lifted onto a ship and a process in which the following operation is performed after the seabed sediment is raised on the ship, a material such as gas hydrate may be dissociated, and a material gasified in the core increases, such that a gas layer may be formed in the core due to expansion of the gas. (The gas is collected at one point, and the sediment is pushed out at the point at which the gas is collected, such that the gas layer is generated.)

Since the origin of the gas, carbon cycle, whether or not petroleum, natural gas, and gas hydrate are present, and the like may be recognized through the gas of the gas layer generated in the core, it is very important work to analyze the gas in the core. This work should be significantly rapidly performed.

In addition, the gas should be significantly cautiously handled in order to increase accuracy of an analysis. For example, a contact between the gas and a material such as air, or the like, should be minimized, and the gas should be stored at a cold temperature.

However, according to the related art, when the gas is extracted from the gas layer in the drilled core, a scheme of mounting a gap gas collector, inserting a syringe into the drilled core to suck the gas, and then filling a predetermined storing container (a glass vial, or the like) with the gas was used, such that a long time was required. In addition, since the gas stored in the predetermined container was moved for a long time and then analyzed on land (using gas chromatography, or the like), reliability was reduced. (Since the drilled core for extracting the gas is made of a soft material, a needle of the syringe may be injected into the drilled core.)

RELATED ART DOCUMENT

Patent Document (Patent Document 1) Korea Patent No. 10-1048528
(Patent Document 2) Korea Patent No. 10-0978143

SUMMARY

An embodiment of the present invention is directed to providing an apparatus for extracting, analyzing, and storing gas in a drilled core on a ship, capable of improving reliability of an analysis by rapidly extracting and analyzing gas from a gas layer in the drilled core and storing remaining gas, when a seabed sediment extracted through a seabed sediment drilling apparatus is lifted in a state in which it is filled in the drilled core.

According to an exemplary embodiment of the present invention, a needle is inserted in a drilled core to allow gas to be supplied to gas analyzing apparatuses positioned on a ship, particularly to be supplied at a predetermined pressure by a valve, and the gas is supplied to the gas analyzing apparatuses or a storing container by the first 3-way valve 30, such that the gas in the drilled core may be rapidly extracted and analyzed and remaining gas may also be stored, thereby making it possible to improve reliability of an analysis.

An apparatus according to the exemplary embodiment of the present invention includes a needle for core insertion inserted into the drilled core to allow the gas in the drilled core to be discharged to the outside.

In addition, the apparatus according to the exemplary embodiment of the present invention includes a first 3-way valve into which the gas passing through the needle for core insertion is introduced and which controls the introduced gas so as to be supplied to a gas storing container or gas analyzing apparatuses positioned on a ship.

DETAILED DESCRIPTION OF MAIN ELEMENTS

Figure 1:
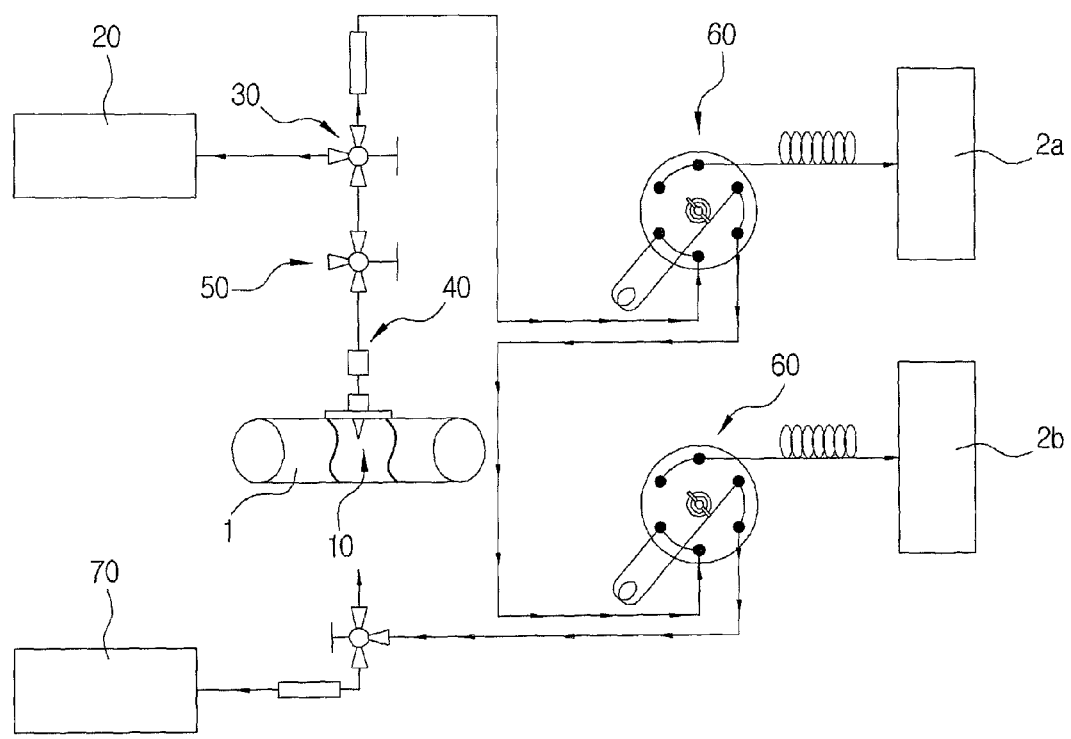
FIG. 1 is a general schematic view for explaining an apparatus for extracting, analyzing, and storing gas in a drilled core on a ship according to an exemplary embodiment of the present invention.
Figure 2:
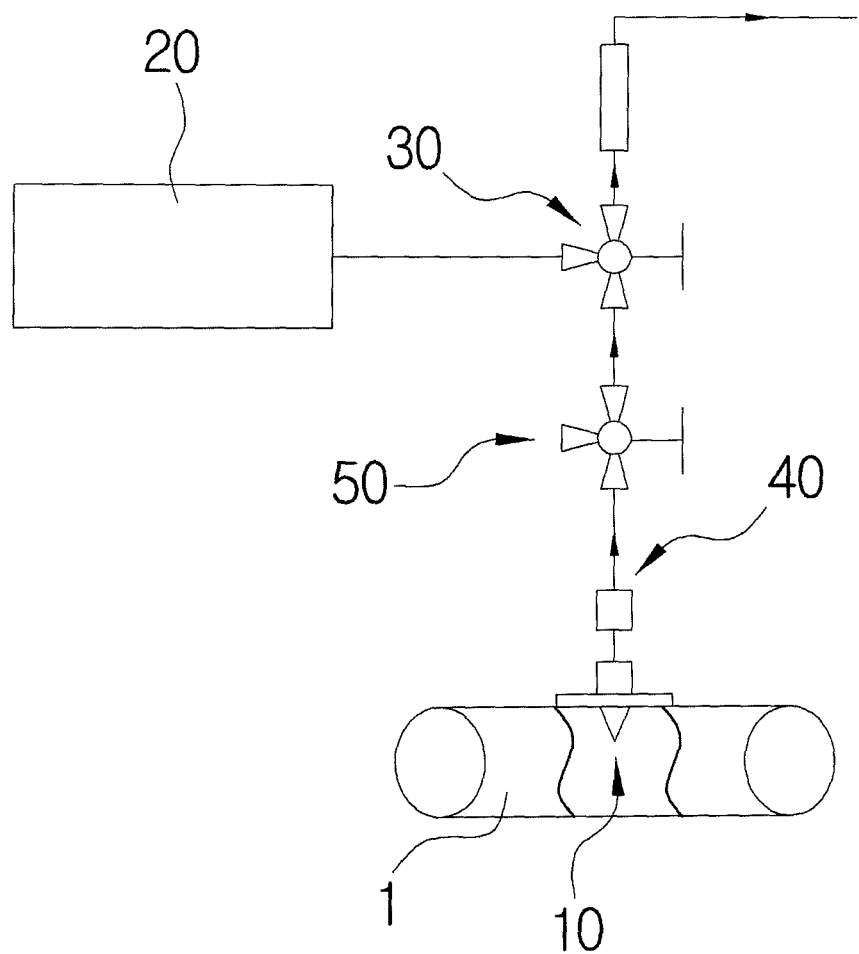
FIG. 2 is a schematic view for explaining a state in which the gas in the drilled gas is moved to a gas analyzing apparatus through a first 3-way valve.
Figure 3:
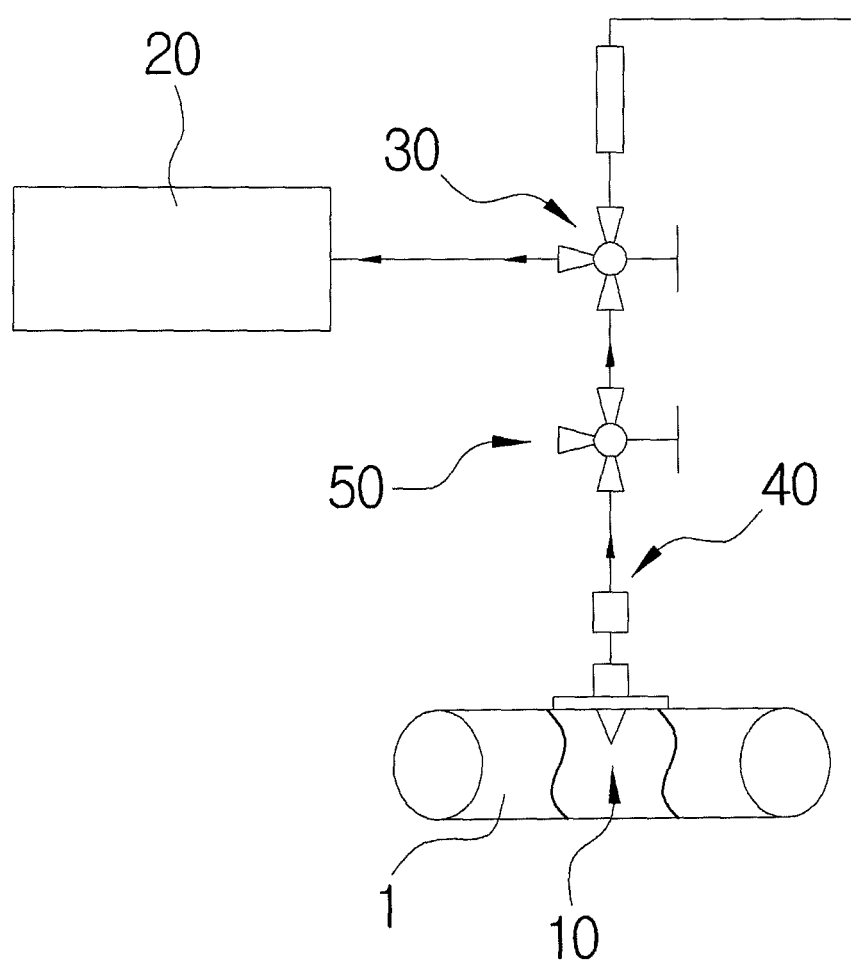
FIG. 3 is a schematic view for explaining a state in which the gas in the drilled gas is moved to a gas storing container through the first 3-way valve.
Figure 4:
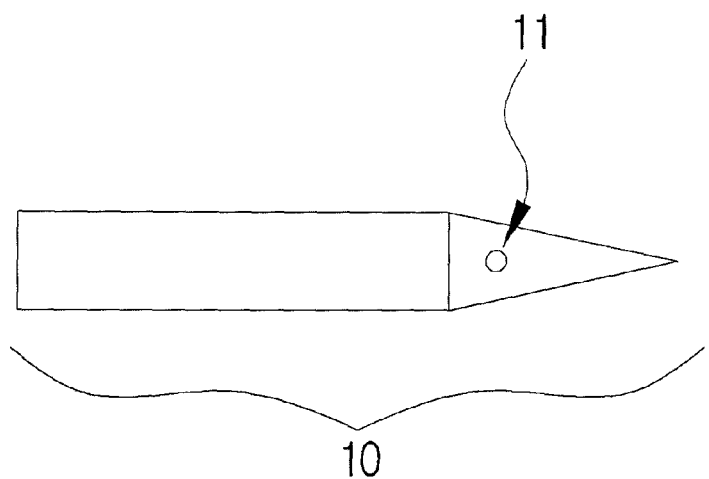
FIG. 4 is a schematic view for explaining a gas introducing hole formed in a needle for core insertion according to the exemplary embodiment of the present invention.

1: Drilled Core
2a, 2b: Gas Analyzing Apparatus
10: Needle for Core Insertion
11: Gas Introduction Hole
20: Gas Storing Container
30: First 3-way Valve
40: Pressure Controlling Valve
50: Second 3-way Valve
60: Analysis Channel Determining Unit
70: Storing Container

DETAILED DESCRIPTION OF EMBODIMENTS

Hereinafter, the technical spirit of the present invention will be described in more detail with reference to the accompanying drawings.

However, the accompanying drawings are only an example shown for explaining in more detail the technical idea of the present invention and therefore, the technical idea of the present invention is not limited to the accompanying drawings.

An object the present invention is to provide an apparatus for extracting, analyzing, and storing gas in a drilled core on a ship, capable of improving reliability of an analysis by rapidly extracting and analyzing gas from a gas layer in the drilled core and storing remaining gas, when a seabed sediment extracted through a seabed sediment drilling apparatus is lifted in a state in which it is filled in the drilled core.

To this end, the apparatus according to the exemplary embodiment of the present invention includes the needle 10 for core insertion inserted into a drilled core 1 to allow gas in the drilled core 1 to be discharged to the outside.

In addition, the apparatus according to the exemplary embodiment of the present invention includes the first 3-way valve 30 into which the gas passing through the needle 10 for core insertion is introduced and which controls the introduced gas so as to be supplied to a gas storing container 20 or gas analyzing apparatuses 2a and 2b positioned on a ship.

That is, after the gas positioned at a gas layer of the drilled core 1 passes through the needle 10 for core insertion, the gas may be supplied to and stored in the gas storing container 20 by the first 3-way valve 30 or be supplied to and analyzed in the gas analyzing apparatuses 2a and 2b.

However, only with the configuration as described above, it is significantly difficult to smoothly analyze and store the gas.

Particularly, it is difficult to extract, analyze, and store high-quality gas and it is possible to have a significant influence on a seabed sediment in the drilled core 1 at the time of extraction of the gas.

That is, when the gas rapidly exits from the gas layer of the drilled core 1, the seabed sediment pulled out to an outer side of the gas layer flows into the gas layer, such that the gas layer becomes turbid.

As a result, the good-quality gas may not be extracted, analyzed, and stored.

Further, in the case in which a pressure of the gas supplied to the gas analyzing apparatuses 2a and 2b exceeds a set range, a fault is generated in the gas analyzing apparatuses and reliability of the analysis is reduced.

In order to solve this problem, the apparatus according to the exemplary embodiment of the present invention further includes a pressure controlling valve 40 allowing the gas to be discharged at a pressure in a predetermined range when the gas is discharged to the first 3-way valve 30 through the needle 10 for core insertion.

The pressure controlling valve 40 capable of controlling a pressure of a moved fluid in a set range has been applied to various industrial fields.

The needle 10 for core insertion, which is a component according to the exemplary embodiment of the present invention, is provided with a gas introduction hole 11 formed so that the gas in the drilled core 1 is introduced thereinto in order to be discharged to the outside.

A blocking phenomenon of this gas introduction hole 40 needs to be prevented.

To this end, the gas introduction hole 11 may be formed at a side of the needle 10 for core insertion as shown in the accompanying drawings.

In the case in which the gas introduction hole is formed at the side of the needle 10 for core insertion, a phenomenon that the gas introduction hole 11 is blocked by the seabed sediment in a process of inserting the needle 10 for core insertion into the drilled core 1 is prevented.

When the apparatus according to the exemplary embodiment of the present invention further includes the second 3-way valve 50 allowing the gas passing through the needle 10 for core insertion to be supplied to the first 3-way valve 30 or to be discharged to the outside, even though the seabed sediment is introduced into the needle 10 for core insertion, the seabed sediment is discharged to the outside through the second 3-way valve 50, thereby making it possible to prevent a path through which the gas is moved from being polluted.

In this structure, a connection pipe connecting the needle 10 for core insertion and the second 3-way valve 50 may be made of a transparent material so that the gas is moved.

That is, it is possible to determine whether the gas is supplied to the first 3-way valve 30 or discharged to the outside while confirming whether foreign materials such as the seabed sediment, or the like, are included in the gas moved to the second 3-way valve 50.

When the apparatus according to the exemplary embodiment of the present invention further includes an analysis channel determining unit 60 allowing the gas passing through the first 3-way valve 30 to be supplied to a predetermined gas analyzing apparatus 2a or 2b among a plurality of gas analyzing apparatuses 2a and 2b, various analysis data may be rapidly secured through the plurality of gas analyzing apparatuses 2a and 2b.

This analysis channel determining unit 60, which generally has a form of a multi-directional valve, has been generally used in an apparatus for analyzing gas. According to the exemplary embodiment of the present invention, an analysis channel determining unit having the same form as that of the analysis channel determining unit according to the related art may be used.

According to the exemplary embodiment of the present invention, the gas storing container 20 may be implemented in a syringe form to slowly discharge the gas stored therein to the outside by moving a piston.

The case in which the gas passing through the needle 10 for core insertion may be supplied to the first 3-way valve 30 or discharged to the outside by the second 3-way valve 50 has been described above.

In this structure, the second 3-way valve 50 is positioned between the needle 10 for core insertion and the first 3-way valve 30 (See FIG. 1).

Figure 5:
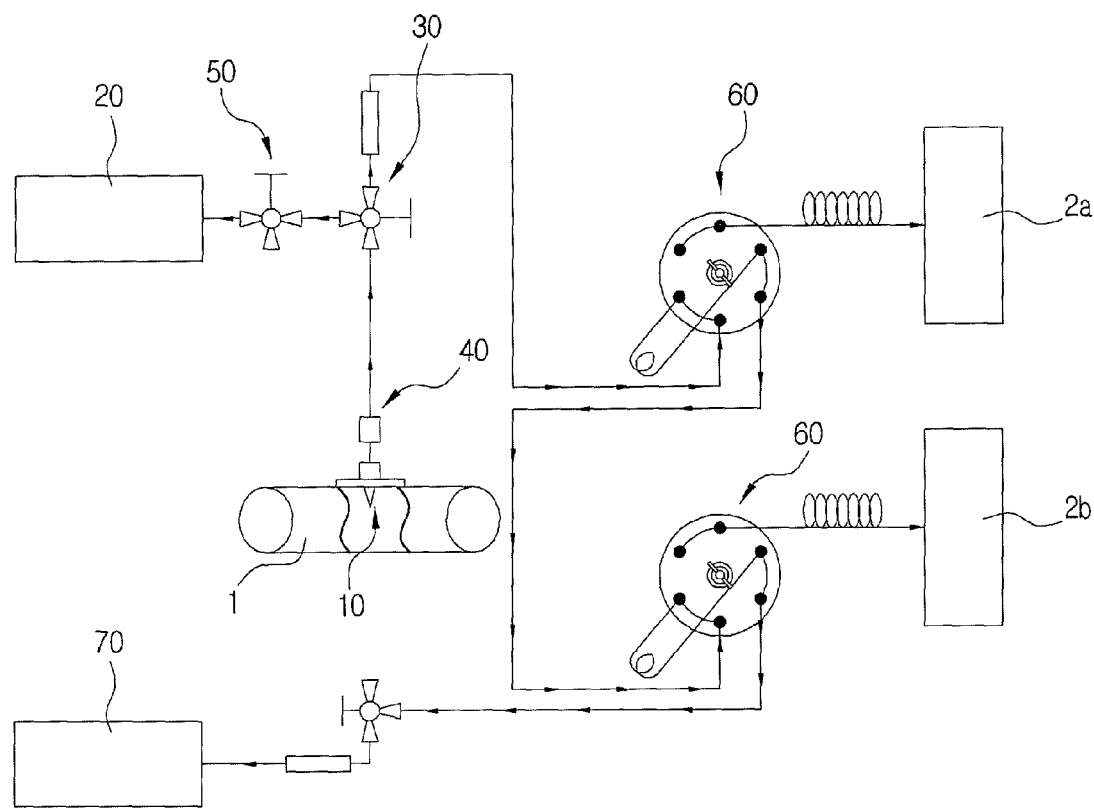
FIG. 5 is a general schematic view for explaining the apparatus for extracting, analyzing, and storing gas in a drilled core on a ship according to an exemplary embodiment of the present invention in which a second 3-way valve is positioned between the first 3-way valve 30 and the gas storing container 20.

However, the second 3-way valve may also be positioned between the first 3-way valve 30 and the gas storing container 20 (See FIG. 5).

In this structure, the gas including the seabed sediment, or the like, is moved to the gas storing container 20 and then discharged.

Therefore, this structure has a disadvantage in that the seabed sediment passes through the first 3-way valve 30.

Although the gas is supplied to the gas analyzing apparatuses 2a and 2b through the first 3-way valve 30 in the exemplary embodiment of the present invention, gas that does not move to the gas analyzing apparatuses by the analysis channel determining unit may also be implemented so as to be stored in a separate storing container 70.

As set forth above, with the apparatus according to the exemplary embodiment of the present invention, since the needle may be inserted into the drilled core to supply the gas to the gas analyzing apparatus positioned on the ship or the gas storing container, the gas is rapidly extracted and analyzed from the gas layer in the drilled core and the remaining gas is stored, thereby making it possible to improve the reliability of the analysis.

Particularly, the pressure controlling valve is provided, such that the gas may exit from the drilled core at a pressure in a predetermined range. Therefore, a phenomenon that the seabed sediment is mixed with the gas layer in the drilled core may be solved, and the gas may be supplied to the gas analyzing apparatus at the pressure in a predetermined range, such that the analysis may be stably performed.

In the case in which the gas introducing hole formed so that the gas to be discharged to the outside may be introduced into an inner channel of the needle for core insertion is formed at the side of the needle for core insertion, the blocking of the gas introducing hole is prevented, such that the analysis may be more stably performed.

Further, in the case in which the second 3-way valve allowing the gas passing through the needle for core insertion to be supplied to the first 3-way valve or be discharged to the outside is further provided, when the seabed sediment is included in the gas, the seabed sediment is discharged to the outside before arriving at the first 3-way valve, such that the analysis may be stably performed.

What is claimed is:

1. An apparatus for extracting gas from a drilled core, and analyzing and storing the gas, said drilled core being obtained from seabed sediment, the apparatus comprising:
    a needle (10) to be inserted into the drilled core (1) to allow the gas in the drilled core (1) to be discharged to the outside of the drilled core (1);
    a first gas storing container (20);
    gas analyzing parts (2a) and (2b);
    a first 3-way valve (30) into which the gas passed through the needle (10) is introduced and which controls the introduced gas so as to be supplied to the gas storing container (20) or to the gas analyzing parts (2a) and (2b);
    a gas analysis channel determining unit (60) which allows the gas passed through the first 3-way valve to be supplied to one of the gas analyzing parts (2a) or (2b);
    a second gas storing container (70) for storing gas that does not move to the gas analyzing apparatuses by the gas analysis channel determining unit (60);
    a second 3-way valve (50) positioned between the needle (10) for core insertion and the first 3-way valve (30) to allow the gas passing through the needle (10) for core insertion to be supplied to the first 3-way valve (30) or to be discharged to the outside; and
    a connection pipe connecting the needle (10) for core insertion and the second 3-way valve (50) and made of a transparent material,
    wherein the needle (10) is provided with a gas introduction hole (11) on the side of the needle, through which the gas in the drilled core (1) flows into the needle.

2. The apparatus of claim 1, further comprising a pressure controlling valve (40) allowing the gas to be discharged, at pressure in a predetermined range, from the drilled core (1) to the first 3-way valve (30) through the needle (10), wherein the pressure controlling valve (40) is connected to the needle (10) and to the first 3-way valve.

* * * * *